United States Patent
Maitrejean et al.

(10) Patent No.: US 7,834,989 B2
(45) Date of Patent: Nov. 16, 2010

(54) LUMINESCENCE IMAGINING INSTALLATION AND METHOD

(75) Inventors: Serge Maitrejean, Paris (FR); Emilie Roncali, Paris (FR); Quentin Le Masne De Chermont, Paris (FR)

(73) Assignee: Biospace Lab, Paris (FR)

( * ) Notice: Subject to any disclaimer, the term of this patent is extended or adjusted under 35 U.S.C. 154(b) by 239 days.

(21) Appl. No.: 12/048,052

(22) Filed: Mar. 13, 2008

(65) Prior Publication Data

US 2009/0066960 A1 Mar. 12, 2009

(30) Foreign Application Priority Data

Sep. 10, 2007 (FR) .................................. 07 06327

(51) Int. Cl.
*G01N 21/00* (2006.01)
(52) U.S. Cl. ....................................................... 356/73
(58) Field of Classification Search ........................ None
See application file for complete search history.

(56) References Cited

U.S. PATENT DOCUMENTS

| | | | | |
|---|---|---|---|---|
| 7,109,483 | B2* | 9/2006 | Nakasuji et al. ............. | 250/310 |
| 7,113,217 | B2 | 9/2006 | Nilson et al. | |
| 7,298,415 | B2 | 11/2007 | Nilson et al. | |
| 7,352,463 | B2* | 4/2008 | Bounaix .................... | 356/437 |
| 2003/0193517 | A1 | 10/2003 | Cable | |
| 2004/0021771 | A1 | 2/2004 | Stearns | |
| 2005/0028482 | A1 | 2/2005 | Cable et al. | |
| 2005/0149877 | A1 | 7/2005 | Rice et al. | |
| 2005/0201614 | A1 | 9/2005 | Rice et al. | |
| 2005/0237423 | A1 | 10/2005 | Nilson et al. | |
| 2006/0203243 | A1 | 9/2006 | Nilson et al. | |
| 2006/0250517 | A1 | 11/2006 | Nilson et al. | |
| 2006/0250518 | A1 | 11/2006 | Nilson et al. | |
| 2006/0268153 | A1 | 11/2006 | Rice et al. | |
| 2007/0016078 | A1 | 1/2007 | Hoyt | |
| 2007/0080305 | A1 | 4/2007 | Maitrejean | |
| 2007/0244395 | A1 | 10/2007 | Wang et al. | |
| 2007/0253908 | A1 | 11/2007 | Rice et al. | |
| 2008/0018899 | A1 | 1/2008 | Stearns et al. | |
| 2008/0031494 | A1 | 2/2008 | Rice et al. | |
| 2008/0051665 | A1 | 2/2008 | Xu et al. | |
| 2008/0052052 | A1 | 2/2008 | Stearns et al. | |

FOREIGN PATENT DOCUMENTS

| | | |
|---|---|---|
| EP | 1 806 575 | 7/2007 |
| WO | WO03/006966 | 1/2003 |
| WO | WO2004/008123 | 1/2004 |
| WO | WO 2005/043138 | 5/2005 |
| WO | WO2006/062914 | 6/2006 |
| WO | WO2006/122229 | 11/2006 |
| WO | WO2007/080326 | 7/2007 |
| WO | WO2007/130369 | 11/2007 |
| WO | WO2008/024986 | 2/2008 |
| WO | WO2008/025006 | 2/2008 |

OTHER PUBLICATIONS

International Search Report from counterpart application No. PCT/EP2008/061963; Report dated Dec. 17, 2008.
French Preliminary Search Report; European Patent Office; Jun. 9, 2008 ;EPO Form 1503.
French Written Opinion; European Patent Office; Sep. 10, 2008.
U.S. Appl. No. 60/756,036, filed Feb. 24, 2006, Cong, et al.
Milstein, et al.; *Fluorescence optical diffusion tomography*; Applied Optics, Jun. 1, 2003 pp. 3081-3094; vol. 42, No. 16.

(Continued)

*Primary Examiner*—Tu T Nguyen
(74) *Attorney, Agent, or Firm*—Miller, Matthias & Hull

(57) ABSTRACT

A luminescence imaging installation is disclosed comprising a lightproof enclosure containing: a support receiving a sample to be imaged; a detector detecting a luminescence image from the sample to be imaged; and a light reflector device reflecting light towards the detector The light reflector device surrounds the support at least in part and presents at least two portions that are inclined relative to each other, each reflecting light towards the detector.

27 Claims, 6 Drawing Sheets

OTHER PUBLICATIONS

Kuo, et al.; *Three-dimensional reconstruction of in vivo bioluminescent sources based on multispectral imaging*; Journal of Biomedical Optics Mar./Apr. 2007; vol. 12(2); pp. 024007-1/-12.

Wang, et al.; *The First Bioluminescence Tomography System for Simultaneous Acquisition of Multiview and Multispectral Data*; International Journal of Biomedical Imaging; vol. 2006, Article ID 58601: pp. 1-8, 2006.

Ripoll, et al. *Kirchhoff approximation for diffusive waves*; Physical Review E, vol. 64, 051917, 051917-1-051917-8, 2001.

* cited by examiner

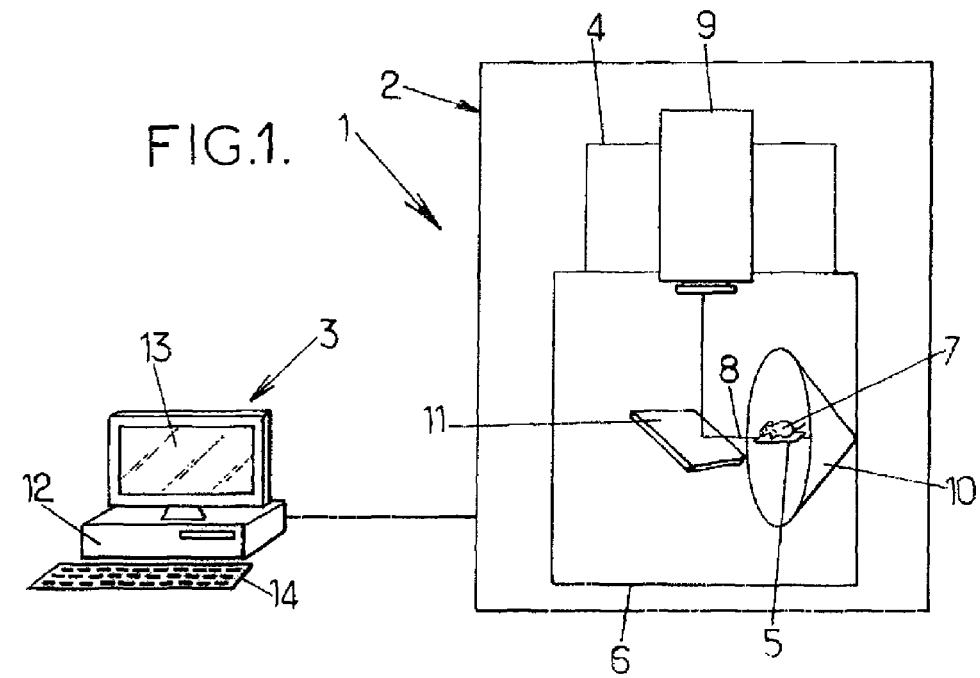
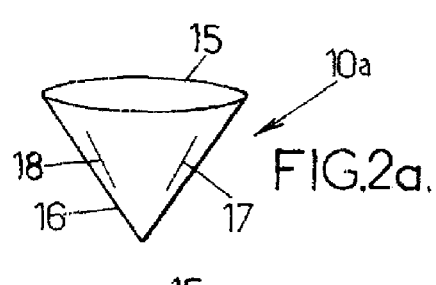
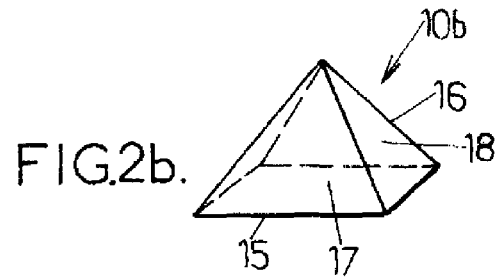
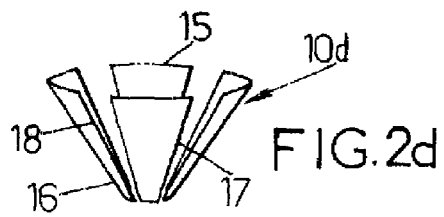
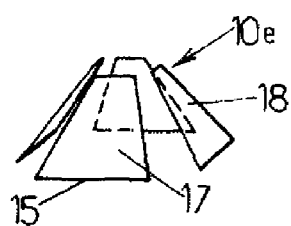
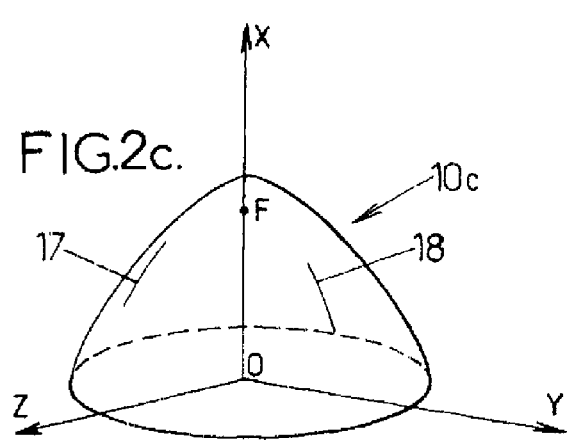

LUMINESCENCE IMAGING INSTALLATION AND METHOD

FIELD OF THE DISCLOSURE

The present invention relates to luminescence imaging installations and methods.

BACKGROUND OF THE DISCLOSURE

More particularly, the invention relates to a luminescence imaging installation comprising a lightproof enclosure containing a support adapted to receive a sample to be imaged;
a detector adapted to detect a luminescence image from the sample to be imaged, corresponding to a light signal emitted from the inside of the sample; and
a light reflector device for reflecting light towards the detector.

Document US 2005/237423 describes an example of such an installation. In that example, in order to obtain a sufficiently complete representation of the luminescence emission from the small laboratory animal, the animal is caused to turn inside the installation so as to take a plurality of successive images under a plurality of orientations.

If the small laboratory animal is anesthetized while images are being taken, there is indeed no difficulty in taking a plurality of images in different orientations, and in obtaining therefrom a faithful representation of its surface, one that might possibly be suitable for being displayed in three dimensions, since the animal is stationary throughout the duration of the photographic acquisition.

Nevertheless, it is sometimes desirable not to anesthetize small laboratory animals during luminescence imaging, for example if it is desired to image muscular activity, since that can require the small laboratory animal to be in a state of wakefulness.

Furthermore, the device known from the above document presents the drawback that the luminescence signal is detected at distinct instants since the acquisitions of the signal at different angles of incidence take place at successive instants. As a result it is difficult to quantify the detection of the luminescence signal, given that it already varies strongly over time.

A particular object of the invention is to mitigate those drawbacks.

SUMMARY OF THE DISCLOSURE

To this end, according to the invention, an installation of the kind in question is characterized in that the light reflector device surrounds the support at least in part, presenting at least two portions that are inclined relative to each other, each reflecting light from the support towards the detector.

By means of these dispositions, a luminescence signal emitted by the sample is acquired simultaneously over a large solid angle.

In certain embodiments of the invention, it is optionally possible also to have recourse to one or more of the following dispositions:

the light reflector device presents at least in part the shape of a quadric;
the light reflector device presents at least in part the shape of a cone having a cone axis, the light reflector device and the support being so placed as to have the sample lying along the cone axis the cone presents a base and a generator line, the base presenting a shape selected from:
at least in part a conic;
at least in part a polygon;
the light reflector device presents the shape of a paraboloid presenting a focus, the light reflector device being placed in such a manner that the focus is disposed in the vicinity of the support;
the support is transparent and the reflector device presents portions disposed on either side of the support;
the installation includes a locating device adapted to generate a locating light signal on the surface of the sample, the detector being adapted also to detect a positioning light signal obtained by the locating signal being reflected by the sample and then by the reflector device;
the detector comprises a luminescence detector adapted to detect both the luminescence image and the positioning light image;
the detector comprises a luminescence detector adapted to detect the luminescence image, and a positioning detector distinct from the luminescence detector, and adapted to detect the positioning light image;
the imaging installation comprises a separator device adapted to separate the luminescence image from the positioning light image; the installation includes a drive member adapted to move the locating light signal;
the imaging installation comprises a transillumination device adapted to generate a transillumination light signal to be applied on a first surface of the sample, whereby the transillumination light signal is scattered inside the sample and forms a luminous spot (35) on the sample opposite said first surface and from which a transmitted light signal radiates, the detector being adapted to detect the transmitted light signal;
the transillumination device is adapted to generate said light signal emitted from the inside of the sample, by exciting fluorescence of fluorescent probes contained inside the sample;
the locating device and the transillumination device are a single device adapted to generate both the locating light signal and the transillumination light signal;
the single device is adapted to generate a single signal which serves both as the locating light signal and the transillumination light signal;
the installation further comprises a processing computer unit connected to the detector;
the processing computer unit has a memory zone containing a positioning image previously acquired by detecting a positioning signal obtained by reflection of a locating signal on the sample and then on the reflector device; and
the processing computer unit includes a computer adapted to obtain an image associating each geometrical zone of the sample with a value of luminescence in said zone from the positioning image and the detected luminescence image;
each geometrical zone of the sample is a surface zone of the sample;
the computer is also adapted to associate a luminescence value with each of a plurality of geometrical volume zones inside the sample from respective luminescence values associated with each geometrical surface zone;
each geometrical zone of the sample is a volume zone of the sample; and
the processing computer unit has a memory zone containing a transillumination image previously obtained by detecting a transmitted light signal obtained by scattered transmission of a transillumination light signal applied onto the sample; said computer is adapted to obtain an image associating each volumic zone inside the sample with a value of luminescence in said zone from the detected luminescence image and the transillumination image; the processing computer is adapted to obtain optical characteristics of the inside of the sample from the transillumination image, and to obtain the image associating each volumic zone inside the sample with a value of luminescence in said zone from the luminescence image and the optical characteristics;

the light reflector device surrounds the support over a solid angle of not less than $\pi$.

In another aspect, the invention provides a luminescence imaging method in which an imaging installation is provided comprising a lightproof enclosure containing:

a support adapted to receive a sample to be imaged;

a detector placed in an acquisition region and adapted to detect a luminescence image of the sample to be imaged; and a light reflector device for reflecting light towards the detector;

in which the support is provided with a sample to be imaged, and in which the detector detects a luminescence image of the sample to be imaged, corresponding to a light signal emitted from inside the sample, the method being characterized in that the light reflector device surrounds the support at least in part, presenting at least two portions that are inclined relative to each other, each reflecting light coming from the sample towards the detector, In certain implementations, it is optionally possible to have recourse to one or more of the following dispositions;

a processing computer unit connected to the detector has a memory zone containing a positioning image previously acquired by detecting a positioning signal obtained by a locating signal being reflected by the sample and then by the reflector device; and there is obtained an image associating, for each geometrical zone of the sample, a luminescence value for said zone, from the positioning image and the detected luminescence image; prior to acquiring the luminescence signal, a positioning signal obtained by reflecting a locating signal on the sample and then on the reflector device is detected and stored in the memory zone;

the positioning image is periodically updated by detection of positioning signals simultaneously with acquiring the luminescence signal;

a processing computer unit connected to the detector has a memory zone containing a transillumination image previously obtained by detecting a transmitted light signal obtained by scattered transmission of a transillumination light signal applied onto the sample, wherein an image associating each volumic zone inside the sample with a value of luminescence in said zone is obtained from the detected luminescence image and from the transillumination image;

prior to acquiring the luminescence signal, a transmitted signal obtained by scatterly transmitting inside the sample a transillumination signal applied onto the sample is detected and stored in the memory zone;

a transillumination signal is generated onto the sample, the transillumination signal exciting fluorescence of fluorescent probes contained inside the sample, said fluorescence generating the luminescence signal.

According to another aspect, there is provided a computer program product comprising a computer program adapted, when executed on a programmable device, to implement a method comprising obtaining, for each geometrical zone of a sample to be imaged, a luminescence value for said zone from a previously acquired positioning image, corresponding to the detection of a positioning signal obtained by the reflection of a locating signal by the sample and then by a reflector device at least in part surrounding the sample and presenting at least two portions that are inclined relative to each other and each reflecting light coming from the sample toward a detector, and from a luminescence image of the sample corresponding to a light signal emitted from within the sample.

BRIEF DESCRIPTION OF THE DRAWINGS

Other characteristics and advantages of the invention appear from the following description of embodiments thereof, given by way of non-limiting example and with reference to the accompanying drawings.

In the drawings:

FIG. 1 is a diagrammatic view of an imaging installation;

FIGS. 2a to 2e are diagrammatic perspective views of embodiments of reflecting devices for the FIG. 1 installation;

DETAILED DESCRIPTION OF THE DISCLOSURE

Figure 3:
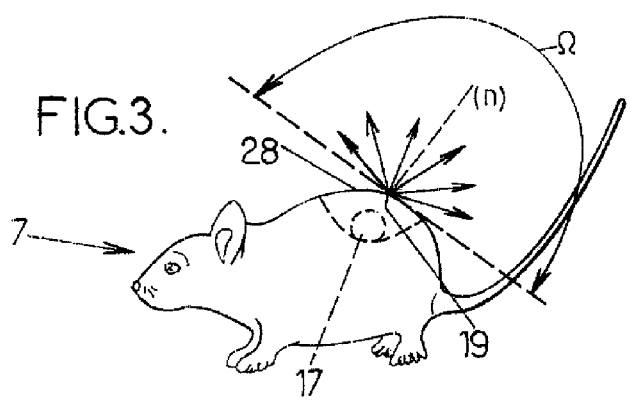
FIG. 3 is a diagrammatic view showing light emission from inside a small laboratory animal.

FIG. 1 is a diagram showing a luminescence imaging installation 1 comprising an imaging box 2 connected to a processing computer unit 3.

The box 2 mainly comprises a lightproof enclosure 4 having a door (not shown) through which it is possible to access the inside of the enclosure, the enclosure being lightproof when the door is in its closed position. The enclosure includes a support 5, e.g. mechanically secured to the floor 6 of the enclosure, and on which a small laboratory animal 7 can be placed. Light radiation 8 is emitted from inside the small laboratory animal 7. By way of example, this light radiation is a luminescence signal representative of a chemical reaction occurring inside the animal, and it may serve as a tracer for such a chemical reaction. The light radiation may also serve to quantify the expression of a given gene carried by the animal and which, on being expressed, gives rise to the above-mentioned chemical reaction. By way of purely illustrative example, the radiation may come from the reaction of a coelenterazine-aequorin photoprotein-substrate pair with a given complementary chemical entity such as calcium coming into the proximity of the photoprotein at axons of the small laboratory animal.

The support 5 may be made to be transparent, so as to make it possible also to detect the emission of luminescence coming from under the body of the small laboratory animal.

In order to detect the luminescence signal emitted by the small laboratory animal 7, a detector 9 is used that is appropriate for detecting such a signal, such as, for example: a cooled charge-coupled device (CCD) camera, an intensified CCD (ICCD) camera, an electron multiplication CCD camera (EMCCD), or some other camera, e.g. presenting one or several million detection cells disposed in columns and rows.

Where appropriate, the installation is used for detecting a phosphorescence signal, or a delayed phosphorescence signal from the small laboratory animal 7.

The installation also has a light reflector device 10 surrounding the small laboratory animal, at least in part. This device is described in greater detail below.

Depending on the relative positions of the small laboratory animal 7 and the detector 9, it should be observed that it is also possible to make use of an optical reflector system comprising, for example, one or more plane mirrors 11 for deflecting the light radiation 8 towards the detector 9.

The processing computer unit 3 comprises a central unit 12 with a processor and a memory zone adapted to store data coming from the detector 9. The memory may also contain some parameter's sent to the box 2 in order to monitor and/or control detection.

The processing computer unit 3 also has a display screen 13 and a control input device 14, such as a keyboard, or some other device. The processor unit 12 is adapted to execute executable computer programs that may be recorded in the processor unit or on a data medium that is removable from said unit.

As shown in FIG. 1, the reflector device 10 surrounds the small laboratory animal 7, at least in part, such that most of the light signals emitted from the small laboratory animal 7 are reflected by the reflector device 10 towards the detector 9 (where appropriate via the deflector mirror 11). The term "surrounding" the sample, is used to mean that the reflector device 10 has at least two portions each reflecting light towards the detector 9, said light reaching said portions from the small laboratory animal, and the portions being inclined relative to each other.

A small number of purely illustrative examples of suitable reflector devices are described with reference to FIGS. 2a to 2e.

In a first example, shown in FIG. 2a, the reflector device 10 is in the form of a truncated cone 10a presenting an open circular base 15 and a rectilinear generator line 16. Two generator lines 17 and 18 form two examples of portions that are inclined relative to each other. In some examples, the angle at the center of the cone may be 30° or 45°, The cone can for example be placed so that the sample lies about the axis of the cone.

In another example shown in FIG. 2b, the light reflector device is made in the form of a pyramid-shaped cone 10b presenting an open base 15 in the form of a quadrilateral and having a rectilinear generator line. Two walls 17 and 18 form two examples of portions that are inclined relative to each other.

Thus, any type of cone, e.g., of base 15 that is conical or polygonal in shape, can be used as the reflector device 10 in the context of the invention. It is preferable to select a shape that is easy to manufacture.

As shown in FIG. 2c, in another embodiment, the reflector device may be constituted, for example, by a paraboloid of revolution 10c having its focus F situated close to the small laboratory animal. Other quadrics could be used to define reflector devices.

It will be understood that although an entire truncated cone is shown as an example of a reflector device 10 in FIG. 1, it is possible to use, for example, only the top half of the truncated cone of FIG. 1, or any other suitable portion of a truncated cone. This naturally applies to any shape for a reflector device 10, such as the shape in the examples shown in FIGS. 2a to 2c.

In the examples shown on FIGS. 2a to 2c, an integral continuous part of the reflector device 10 comprises the two portions inclined with respect to one another. In other embodiments, as shown on FIGS. 2d and 2e, respectively based on FIGS. 2a and 2b, the two inclined portions could be provided on separate parts, discontinuous from one another, of the reflector device 10d, 10e.

The reflector device of the various embodiments is held in position relative to the sample by a not-shown supporting basis fixed to the enclosure.

As shown in FIG. 3, for luminescence imaging, the small laboratory animal 7 has one or more internal light sources 17 (only one is shown in FIG. 3) that emits light in all directions. A portion of this light reaches the outside surface 18 of the sample. Seen from the outside, it appears as though it is the corresponding zone of the outside surface that is emitting luminescence radiation over a solid angle $\Omega=2\pi$ around the normal (n) to the outside surface 28 at the surface emission point 19. The emission 39 of light radiation from the surface emission point 19 can thus be characterized by five geometrical parameters, three of which relate to the three-dimensional position of the point 19 in the frame of reference of the acquisition machine (e.g. expressed as rectangular, cylindrical, or other coordinates), and two of which relate to the orientation of the normal (n) to the outside surface 28 at said point.

Figure 4:
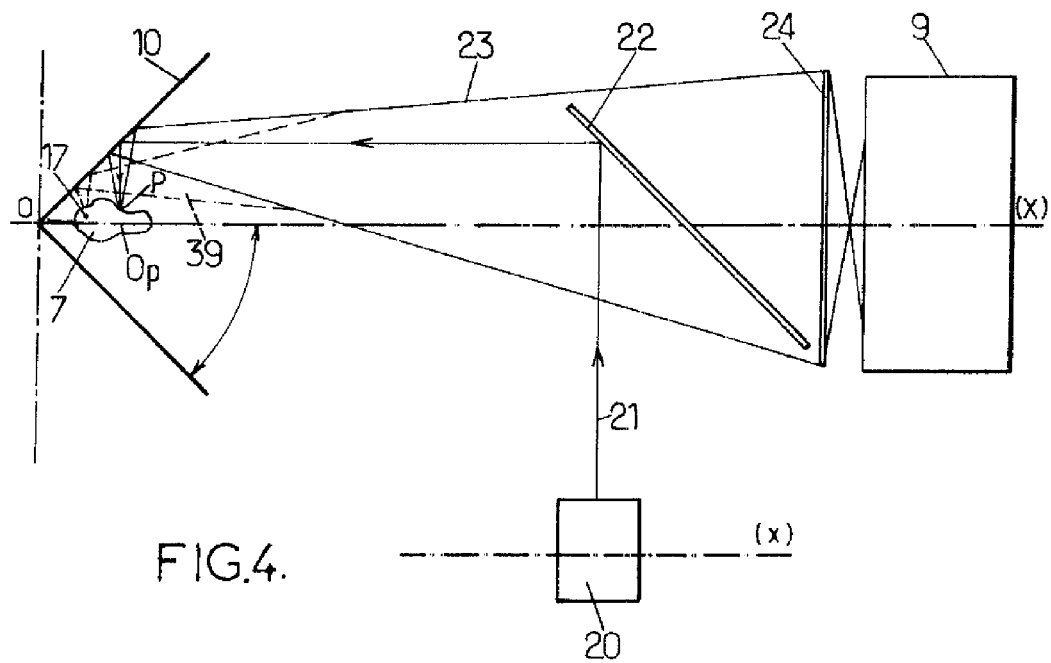
FIG. 4 is a diagrammatic plan view of a positioning step.

As shown in FIG. 4, a locating device is used for obtaining the impulse responses of the optical system for each point of the small laboratory animal. Each surface emission point of the small animal is characterized by only two geometrical parameters, namely its coordinate along the X axis relative to a reference point O of said axis, and the angle formed in the plane containing the point P and perpendicular to the X axis, between the straight line connecting the point P to the axis and a reference straight line in said plane.

By way of example, the locating device comprises a device that emits light detectable by a detector. Fox example, it is possible to use a LASER 20 emitting a locating light beam 21 towards the small laboratory animal 7. Where appropriate, the locating light beam 21 is reflected on the reflecting surface 10 before reaching the small laboratory animal 7, Depending on the geometrical disposition of the imaging installation, it is also possible to use one or more plane deflector mirrors 22, where appropriate semitransparent mirrors, fox conveying the locating light beam 21 to the small laboratory animal 7. A positioning light signal 23, corresponding to the reflection on the small laboratory animal 7 of the locating light beam 21 at the surface point P is thus emitted by being reflected on the reflector device 10 towards a detector. As a detector for the locating device, it is possible for example to use the detector 9 suitable for detecting a luminescence signal.

The detector thus detects the impulse response of the system for a given position of the laser 20 in the frame of reference of the imaging installation.

The locating light beam 21 can be displaced in any appropriate manner so as to sweep all of the points P of the small laboratory animal 7, e.g. by moving the laser 20 along a translation axis $\underline{x}$, with the position of the laser relative to the imaging box remaining known at all times. The position of the laser 20 serves to determine directly the X coordinate of the point P along the X axis of FIG. 4, and also the angle formed between a reference straight line in the plane orthogonal to the X axis and passing through the point P, and the straight line in said plane passing through the point P and through the point of intersection $O_P$ between said plane and the X axis.

In order to determine the other three geometrical parameters of the emission from the point P, the processing computer unit 3 includes a computer adapted to process the signals detected by the positioning detector.

Figure 5A:
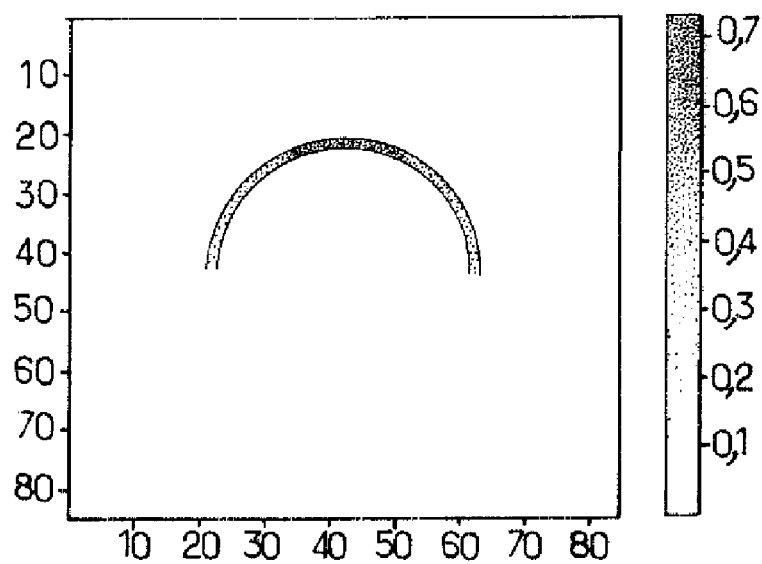
FIGS. 5a and 5b are plane views illustrating a signal detected at a detector for two examples of the position of the positioning signal.

By way of example, FIG. 5a shows the image detected by the detector 9 of the emission from a point P situated on the X axis at a known given distance from the detector, using a reflector device 10 having the shape of half a cone.

Figure 5B:
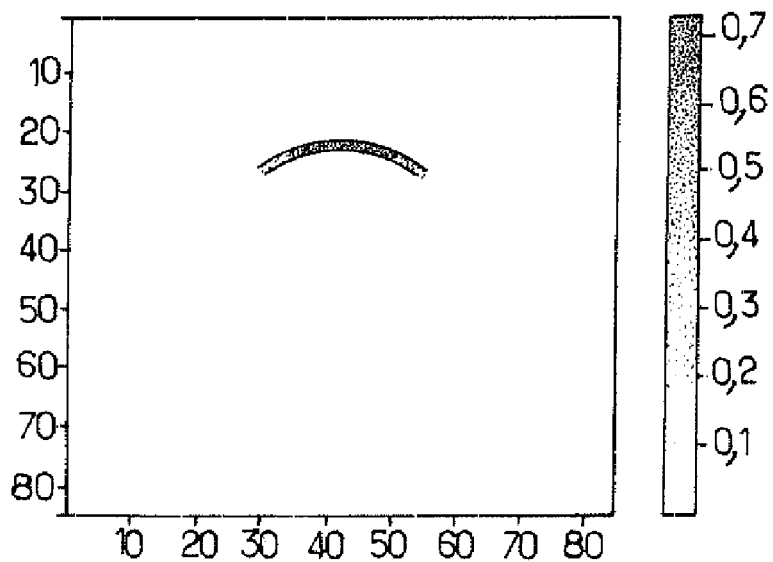

By way of example, FIG. 5b also shows the image obtained at the detector 9 in the same imaging installation of a point P situated at the same X coordinate as the point of FIG. 5a, but at a given, non-zero distance from said axis. In these two examples, the light intensity of the point P is identical.

It is thus possible to store the impulse response of the system corresponding to each point P of the small laboratory animal, and to determine the exact position of the point P in space based on the detected impulse response.

The above-described system operates as follows.

The door of the enclosure is opened and the small laboratory animal 7 that emits light radiation 8 is put into place on the support 5. The door of the imaging box is closed so as to make it lightproof. Where appropriate, photographic acquisition of the small laboratory animal is implemented, e.g. with the detector 9, by illuminating the small laboratory animal with a light source of conventional type.

A locating light beam 21 is caused to be emitted by the laser 20, and the impulse response of the system for a plurality of known positions of the laser 20 is measured, e.g. with the help of the detector 9. These impulse responses are stored in association with the corresponding positions of the laser 20 in the memory of the processing computer unit 3.

A matrix is determined of weight factors $I_{X,\theta}(a,b)$ corresponding of the part of the light detected on the pixel (a,b) which is obtained from the illumination of the point P of coordinates $(X,\theta)$. Hence $\int_{(X,\theta)} I_{X,\theta}(a,b) = 1$.

Using the detector 9, a luminescence image of the small laboratory animal 7 is acquired. As shown in FIG. 1, an image is acquired simultaneously of the luminescence emission 39 from the animal in all directions, with the help of the reflector device 10. Where appropriate, a plurality of successive luminescence images are acquired corresponding to a plurality of distinct detection instants, e.g. if it is desired to evaluate an event that varies over time and that consequently leads to luminescence emission that also varies over time.

These various luminescence images are also stored in the memory means of the processing computer unit 3.

Each detected luminescence image corresponds to a sum of individual images emitted by each of the points P of the small laboratory animal, which can be represented by the following equation:

$$I(A, B) = \int_{(x,\theta)} L(X, \theta) I_{x,\theta}(a, b)$$

in which:
(A,B) are the coordinates of a pixel in the plane of the detector 9;
I(A,B) is the light intensity detected at said pixel in the luminescence image;
$(X,\theta)$ are the coordinates of a point P of the surface of a cylinder equivalent to the small laboratory animal for which it is desired to obtain the light intensity $L(X,\theta)$ emitted at that point;
(a,b) are the coordinates of a pixel of the impulse image detector; and
$I_{X,\theta}(a,b)$ is the dimensional value (or weight) of the light intensity detected by the detector at the pixel of coordinates (a,b) coming from the point P of coordinates $(X,\theta)$.

With I(A,B) stored in the memory as the luminescence image, and $I_{X,\theta}(a,b)$ stored in the memory from the impulse responses for all of the points P, the computer need only solve the above equation by any appropriate method in order to determine $L(X,\theta)$. By way of example, the computer implements an iterative solution algorithm based on statistical methods of the maximum likelihood expectation maximization (MLEM) type.

Further, the computer calculates, based on the impulse responses obtained for each of the $(X,\theta)$ positions, the third geometrical coordinate of the point P of the sample. For example, the memory of the computer comprises previously stored knowledge data related to the detection with the detector of the impulse response obtained from illuminating phantoms of known geometry and location with the locating device, as explained above in relation to FIGS. 5a and 5b. Based on this knowledge data and on the actual impulse response signal detected for the point P, the third geometrical coordinate R (distance of the point P to the reflector device axis) can be calculated.

The three-dimensional surfacic envelope of the sample is hereby determined.

Then $L(X,\theta)$ is projected onto the determined surface envelope. A surfacic 3D image of light emitted from the surface of the sample by luminescence occurring inside the sample is hereby obtained.

It is also possible to store in the memory and/or to show on the screen the surface emission of light that is calculated as being due to luminescence in the small laboratory animal. Where appropriate, this representation is superposed on the previously-acquired envelope of the small laboratory animal, so as to identify anatomically, on the screen, which are the zones that present luminescence emission.

Figure 6:
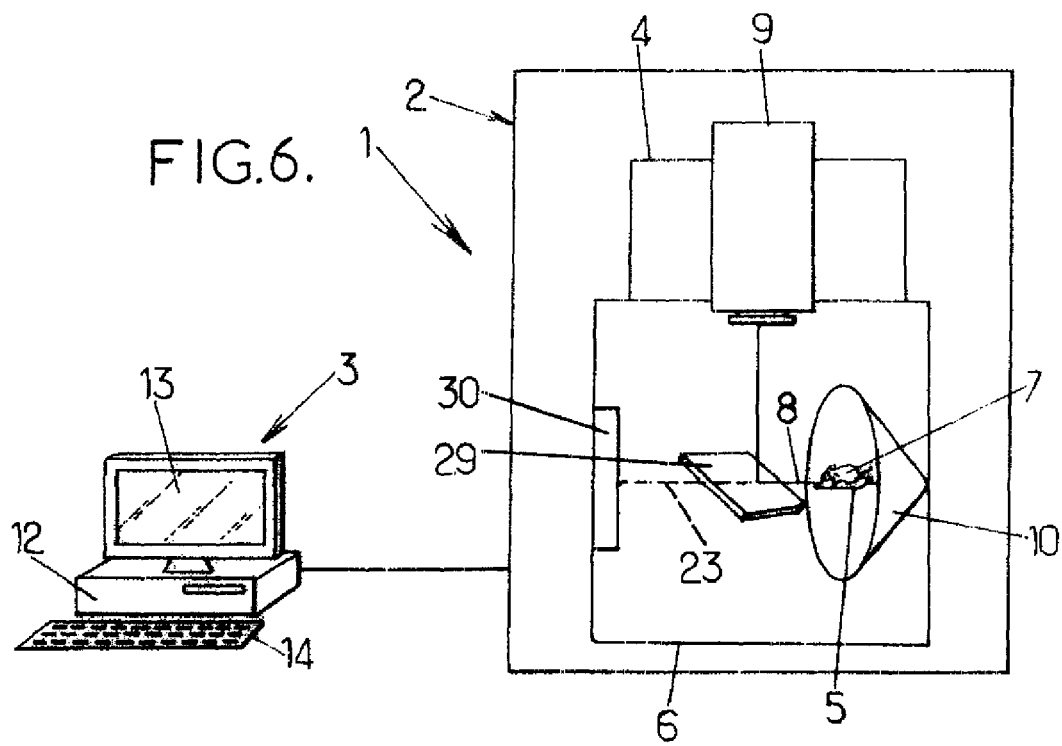
FIG. 6 is a view corresponding to FIG. 1 for a second embodiment of an imaging installation

Another embodiment is shown on FIG. 6. When compared to the embodiment of FIG. 1, the deflector mirror 11 is replaced by a dichroic, or semi-reflective plate 29 adapted to reflect the light signal emitted from within the sample toward the detector 9, and to transmit the positioning light signal 23, which axe of sufficiently different wavelengths. A positioning camera 30, for example of a regular CCD-type, is placed as shown on FIG. 6 so as to detect this positioning light signal.

In this embodiment, it is also possible to use a locating light beam that is pulsed at about video frequency of duration T about some tens of milliseconds. In this variant embodiment, the electronic control unit includes a sequencer which causes the LASER 20 to generate the locating light beam for an ON time to of the time frame T. Generation of the locating light beam is, for example, synchronized with acquisition by the detector of the luminescence signal. In the present embodiment, during the ON time $t_c$, e.g. situated at the start of the time frame T, the locating light beam is emitted towards the stage, so that the positioning light signal 23 reaches the detection apparatus 30.

Figure 7A:
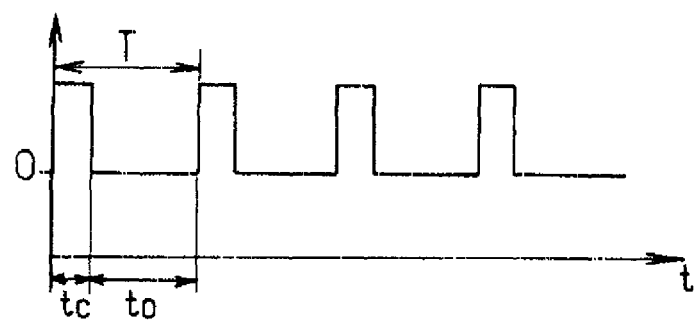
FIG. 7a-7c are graphs showing the states of the locating device, the positioning detector and the luminescence detector, respectively, for an example of use of the second embodiment.
Figure 7B:
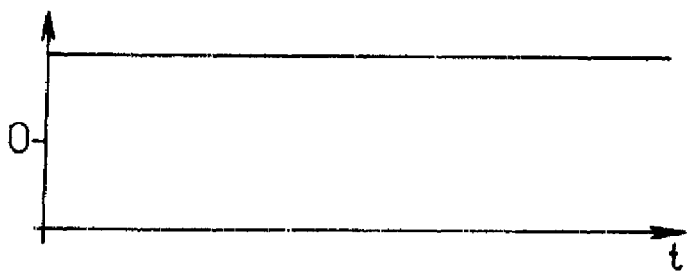
Figure 7C:
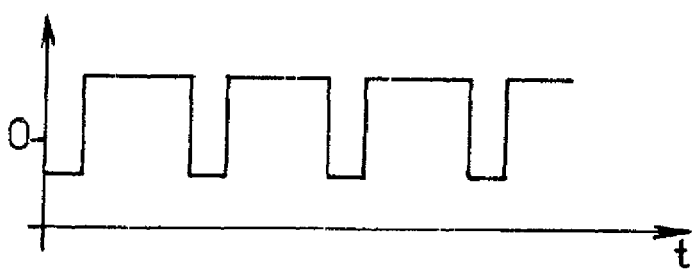

As shown on FIG. 7c, the detector 9 is at that time blinded, so that said detector cannot detect any signal. In order to blind the detector 9, it is possible to use a mechanical shutter situated at the inlet of the detector 9, or electrical shielding is obtained, e.g. by reversing the voltage across the terminals of the detector 9. Then, at the end of time to, the electronic control unit causes the incident illumination to be switched OFF, so that a few instants after $t_c$, only the luminescence coming from the sample 7 is detectable in the enclosure 4. During the OFF time to, the detector 9 is once again in the detection state, and it detects the light signal carrying the luminescence information coming from the sample 7. In this embodiment, the sequencer and the semi-reflective plate 29 are useful as separator devices to separate both signals from one another. It should be noted that, because of the reflection of the luminescent signal toward the detector 9, the fact that, throughout the entire time frame, the sample 7 also emits a signal carrying the luminescence information, has no influence over the signal detected by the positioning detector 30. Indeed, the positioning detector 30 can remain in acquisition mode during the OFF time to, as shown on FIG. 7b, without any significant influence on the measurement performed by said detector.

For the LASER 20, in the above-described variant embodiment, it is also possible to use a light source of spectrum targeted on 800 nanometers, so that autofluorescence, which is inherent to the biological tissues of the sample due to the LASER illumination, is of a wavelength suitable not to be reflected by the dichroic mirror 29 toward the luminescence detector 9, but to rather be transmitted toward the positioning detector 30.

However, it is possible to make provision for the detection by the luminescence detector 9 to take place only after the autofluorescence signal emitted by the sample 7 (even presenting a spectrum superposed on the spectrum of the luminescence signal) has dissipated in the enclosure 4.

The positioning detector 30 thus detects the impulse response of the system for a given position of the LASER. At the following time frame, the LASER is moved so as to displace the locating light beam 21 onto another surfacic point of the sample 7. A positioning image of the sample is obtained from the combined detected positioning signals for the previous acquisition time frames. The positioning image and the detected luminescent image are used to obtain an image associating luminescence data with geometrical zones of the sample as explained above.

This obtention involves a previously acquired positioning image. By "previously acquired", it can be understood that the positioning image is acquired prior to the above obtention calculation but that the positioning image is not necessarily obtained prior to the luminescence acquisition. It could even be obtained during the acquisition of the luminescence signal, for example as explained above in relation to FIGS. 6-7c, or by any other suitable means. It could even be obtained after the acquisition of the luminescence signal.

It should be noted that, once the LASER 20 has scanned the surface of the sample so as to obtain a positioning image thereof, this scan could be repeated, and the data of the positioning image corresponding to a previously acquired detection of a positioning light signal 23 for a given position of the LASER could be discarded and replaced by the data newly acquired for this position of the LASER. In this way, the positioning image is maintained up to date all along the luminescence acquisition.

In all the above embodiments, knowing the distribution of light at each zone corresponding to the surface of the small laboratory animal 7, the computer can also be adapted to determine the locations of the light sources within the sample. During this step, it is desired to associate each internal zone of the volume of the small laboratory animal with a value for the luminescence emitted by said zone. For example, it is possible to implement a method whereby a plurality of virtual zones are defined inside the volume, and given knowledge of the distribution of soft tissue in the animal, e.g., obtained by earlier magnetic resonance imaging or computer tomography of the small laboratory animal, and consequently knowledge of the optical characteristics of each zone, it is possible by solving diffusion equations of light inside the sample, to determine the most likely disposition of the sources within the small animal that would lead to the $L(X,\theta)$ surface distribution of light.

In a variant, the distribution of soft tissue is known from a generic model for the volume of a small laboratory animal, which model is deformed so as to be made to correspond with the locating data concerning the animal being subjected to detection, or by any other suitable method.

Although, in the present example, a two-stage calculation is implemented for determining the surface distribution of light at the surface of the sample from the acquired luminescence image, and then from said surface distribution the position and the intensity of light sources inside the sample, it would be entirely possible to implement a single calculation step during which the volume distribution of sources inside the sample is calculated directly from the luminescence signal detected by the detector 9 without passing via the intermediate calculation of the surface distribution of light.

Figure 8:
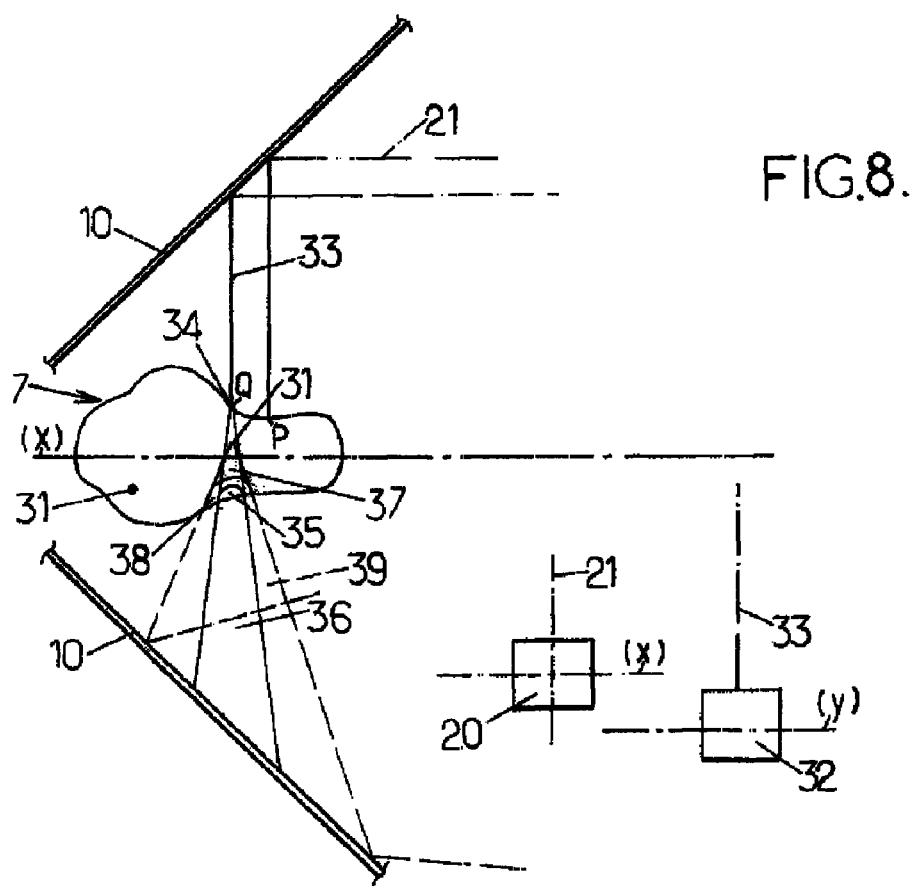
FIG. 8 is a partial view, similar to FIG. 4, of a third embodiment of the invention

A third embodiment of the invention is schematically shown on FIG. 8. According to this embodiment, the imaging installation can be used for fluorescence molecular tomography (FMT). In this mode, the sample internally has fluorescent probes 31 of unknown location and concentration which are to be detected using the imaging installation. Such fluorescent probes 31 generate a fluorescent light signal when excited by a suitable light source. Any kind of fluorescent probes can be used, such as for example, ALEXA FLUOR 680 probes.

According to this embodiment, the installation comprises a transillumination device 32 adapted to generate a transillumination light signal 33 which is directed onto a first surface 34 of the sample 7, for example via reflection onto the mirror 22 (not shown, see FIG. 4) and/or the reflector device 10. The transillumination device 32 is chosen so as to emit a transillumination light signal 33 able to at least partly penetrate into the sample 7 and to be transmitted through the sample 7, Scattering of this signal inside the sample 33 generates a luminescent spot 35 on a second surface of the sample 7 opposite to the first surface 34. A transmitted light signal 36 is thereby generated from the scatterly transmitted transillumination light signal 33 and can be detected by the detector 9, for example, after reflection on the reflector device 10.

In this application, a transillumination device 32 can be chosen so as to generate a transillumination light signal with characteristics which excite the fluorescent probes 31, thereby generating a fluorescent signal 37 with a wavelength different from that of the transillumination signal 33, which is also scattered inside the sample until it reaches the second surface on which it forms a luminescent spot 38. The luminescence of the luminescent probes 31 generates a transmitted light signal 39 emitted from within the sample, to be detected by the detector 9.

For example, the transillumination device 32 is a LASER emitting a signal of wavelength about 690 nm, suitable for exciting the fluorescence of the above-mentioned example of fluorescent probe.

The transillumination light signal 33 can be scanned on the surface of the sample 7, for example, in the same way as the locating signal 21 is.

Figure 9A:
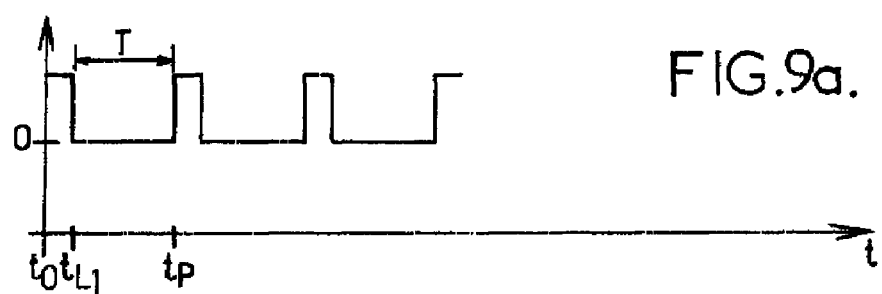
FIGS. 9a and 9b are graphs showing the states of the locating device and the transillumination device, in an example of use of the third embodiment.
Figure 9B:
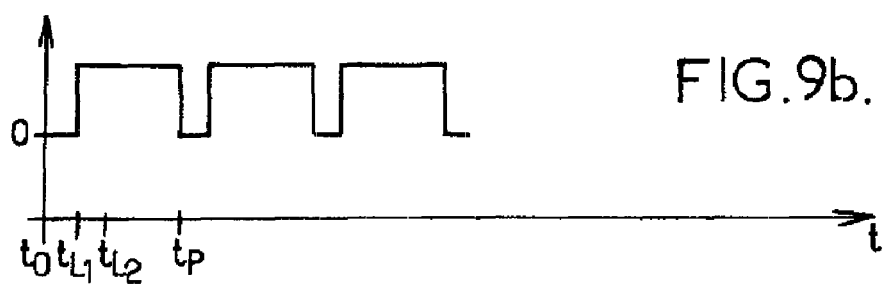

According to this embodiment, as shown on FIG. 9a, between an initial time $t_0$ and a first time $t_{L2}$, the locating light signal is emitted by the locating device, and the corresponding positioning signal is detected by the detector 9 (such as described before and shown for example on FIG. 5a, or 5b) During a second time extending from $t_{L1}$ to $t_{L2}$, a transillumination light signal 33 is emitted by a transillumination device, and the corresponding transmitted light signal 36 is detected by the detector 9, as shown on FIG. 9b.

Figure 10:
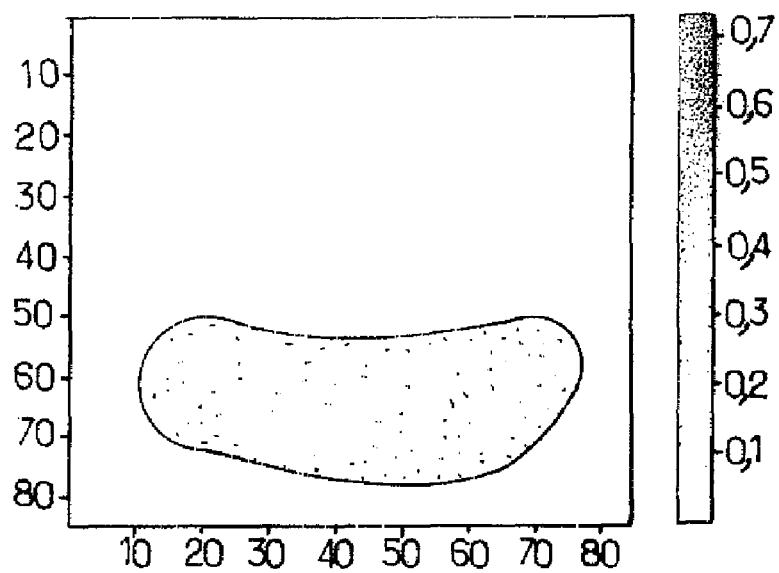
FIG. 10 is a view similar to FIGS. 5a and 5b, of the detection of a transillumination signal for the embodiment of FIG. 8

The detected transmitted light signal is for example shown on FIG. 10.

Then, from a time extending from $t_{L2}$ to $t_F$, emission by the transillumination device is maintained, and a suitable filter is placed on the detection device 9 so as to filter out the transmitted signal. During this time, light emitted from within the sample, corresponding the fluorescent light generated by the excitation of the fluorescent probes by the transillumination device is detected by the detector 9. It should be noted that, between $t_{L1}$ and $t_{L2}$, the fluorescent light signal is weak when compared to the transmitted light signal, and therefore does not impair the detection of the transmitted light signal by the detector 9. Indeed, an attenuation filter (not shown) could be used on the camera between to and $t_{L2}$.

As shown on FIGS. 9a and 9b, these steps are repeated (for example periodically), while scanning a surface of the sample with the locating and the transillumination signals.

As explained above, in relation to the first embodiment, the detection of the positioning signal enables to reconstruct the three-dimensional surface of the sample.

The detected transmitted signal 36 and fluorescent signals are used to determine the position and/or concentration of fluorescent probes inside the sample. The computerized unit is programmed to associate to each volumic zone of the sample 7 a value of fluorescence inside the zone by fluorescence molecular tomography. Many methods are known to obtain this volumic reconstruction and need not be described in more details here. It should be noted that such methods include determining the light scattering optical characteristics of the tissues located inside the sample based on the knowledge of the transillumination light signal emitted onto the first surface of the sample and on the detection of the transmitted light signal, and evaluating from these optical characteristics a most likely source distribution of fluorescent probes inside the sample using light scattering equations in these tissues. An example for solving this problem is for example described in MILSTEIN and Al., "FLUORESCENCE OPTICAL DIFFUSION TOMOGRAPHY", Applied Optics, Jun. 1$^{st}$, 2003, Vol. 42, No. 16, 3081-3094.

Figure 11:
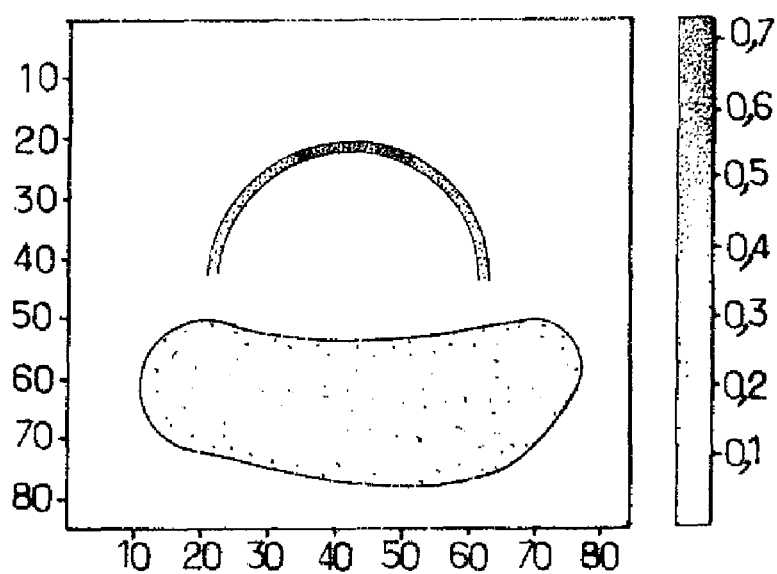
FIG. 11 is a view similar to FIG. 10 of the combined detection of the positioning and the transillumination signal according to a fourth embodiment.

In the above example, the locating device 20 can for example emit a blue/green LASER beam, and be controlled independently of the transillumination device 32 (in the pulsed mode described in relation to FIGS. 9a and 9b). In a fourth embodiment, the locating device 20 and the transillumination device 32 could be performed as a single device, whereby a transillumination light signal 33 is used as a locating signal, the reflection of this signal on the first surface 34 of a sample being detected simultaneously to the transmitted signal such as shown on FIG. 11. The position in space of the LASER 20, 32, enables to easily discriminate, on the detection screen, which part of the detected signal corresponds to the reflected signal, and which part to the transmitted signal. Then, a filter is placed on the camera and the fluorescent light signal is detected under continued illumination by the LASER.

It should be mentioned that the above description is given with a single intensified camera 9. According to a fifth embodiment, FMT could be performed with both intensified camera 9 and a positioning camera 30, such as shown on FIG. 6. In this later case, in this variant embodiment, a semi-reflective device 29 can be used, so that both the positioning signal and the transmitted signal are directed toward the positioning camera 30, whereas the fluorescence signal is directed toward the intensified camera 9. It should be noted that the fifth embodiment contemplates using two independent devices for generating the locating signal and the transillumination signal, such as in the above described third embodiment. However, in a sixth embodiment, the fifth embodiment could be modified by using a single device to generate these two signals, as explained above in relation to the fourth embodiment.

It should be mentioned that, in seventh and eighth embodiments (corresponding respectively to the fifth and sixth embodiment), one does not necessarily need to use a semi-reflective device 29. It would be possible to place both cameras 9 and 30 so as to image a sample 7 along different lines of sight and to use in the computer the known geographical locations of both cameras and of the support 5 so as to calculate corrected images expressed in the same frame of reference, which would be, for example, the frame of reference of one of the cameras 9, 30.

For the above described embodiments of FIGS. 8 to 11, reference to fluorescence molecular tomography is made, whereby the transillumination light signal is used both for generating a transmitted light signal, and exciting fluorescence of the fluorescence probes.

In variant embodiments (for each of the above third to eighth embodiments), the above description could be adapted to imaging luminescent probes. In this case, luminescent probes are used as described above in relation to FIG. 1, instead of the fluorescent probes 31. Such luminescent probes permanently emit light so that the transillumination light signal is not used for exciting them, but only so as to generate a transmitted light signal so as to evaluate the optical characteristics of the inside of the sample. Using the positioning signal to determine the three-dimensional surfacic envelope of the sample, and using the transmitted signal to determine the optical characteristics of the inside of the sample, a three-dimensional image in which for each volumic zone of the sample, a value of luminescence emitted from within the sample, could be determined by any method, by solving the scattering equations of light inside the sample, for example, by the above-described MILSTEIN method.

Although the invention was described with reference to several embodiments, it is understood that it is not limited to these specific embodiments and that these could be combined and/or modified within the scope of the invention.

The invention claimed is:

1. A luminescence imaging installation comprising a light-proof enclosure containing:
    a support adapted to receive a sample to be imaged;
    a detector adapted to detect a luminescence image from the sample to be imaged, corresponding to a light signal emitted from inside of the sample; and
    a light reflector device for reflecting light towards the detector, surrounding the support at least in part, presenting at least two portions that are inclined relative to each other, each reflecting light from the support towards the detector,
    a locating device adapted to generate a locating light signal sweeping points on a surface of the sample, the detector being adapted also to detect a positioning light signal obtained by the locating signal being reflected by one of the points of the sample and then by the reflector device, the installation further comprising a processing computer unit connected to the detector, and having:

a memory zone containing for each point a positioning image previously acquired by detecting said positioning signal, and corresponding to an impulse response of a system for each sample point associated with coordinates of the point in a frame of reference of the imaging installation, and a computer adapted to obtain an image associating each geometrical zone of the sample with a value of luminescence in said zone from the positioning images and the detected luminescence image.

2. An imaging installation according to claim 1, in which the light reflector device presents at least in part the shape of a quadric.

3. An imaging installation according to claim 2, in which the light reflector device presents at least in part the shape of a cone having a cone axis, wherein the light reflector device and the support are so placed as to have the sample lying along the cone axis.

4. An imaging installation according to claim 3, in which the cone presents a base and a generator line, the base presenting a shape selected from:

at least in part a conic;

at least in part a polygon.

5. An imaging installation according to claim 1, in which the light reflector device presents the shape of a paraboloid presenting a focus, the light reflector device being placed in such a manner that the focus is disposed in the vicinity of the support.

6. An imaging installation according to claim 1, in which the support is transparent and the reflector device presents portions disposed on either side of the support.

7. An imaging installation according to claim 1 wherein the detector comprises a luminescence detector adapted to detect both the luminescence image and the positioning light image.

8. An imaging installation according to claim 1 wherein the detector comprises a luminescence detector adapted to detect the luminescence image, and a positioning detector distinct from the luminescence detector, and adapted to detect the positioning light image.

9. An imaging installation according to claim 8 further comprising a separator device adapted to separate the luminescence image from the positioning light image.

10. An imaging installation according to any of claim 1, including a drive member adapted to move the locating light signal.

11. An imaging installation according to claim 1 further comprising a transillumination device adapted to generate a transillumination light signal to be applied on a first surface of the sample, whereby the transillumination light signal is scattered inside the sample and forms a luminous spot on the sample opposite said first surface, whereby a transmitted light signal radiates from the spot, the detector being adapted to detect the transmitted light signal.

12. An imaging installation according to claim 11 wherein the transillumination device is adapted to generate said light signal emitted from the inside of the sample, by exciting fluorescence of fluorescent probes contained inside the sample.

13. An imaging installation according to claim 11 wherein the locating device and the transillumination device are a single device adapted to generate both the locating light signal and the transillumination light signal.

14. An imaging installation according to claim 13 wherein the single device is adapted to generate a single signal which serves both as the locating light signal and the transillumination light signal.

15. An imaging installation according to claim 1, in which each geometrical zone of the sample is a surface zone of the sample.

16. An imaging installation according to claim 15, in which the computer is also adapted to associate a luminescence value with each of a plurality-of geometrical volume zones inside the sample from respective luminescence values associated with each geometrical surface zone.

17. An imaging installation according to claim 1, in which each geometrical zone of the sample is a volume zone of the sample.

18. An imaging installation according to claim 1 wherein the processing computer unit has a memory zone containing a transillumination image previously obtained by detecting a transmitted light signal obtained by scattered transmission of a transillumination light signal applied onto the sample; and wherein said computer is adapted to obtain an image associating each volumic zone inside the sample with a value of luminescence in said zone from the transillumination image and the detected luminescence image.

19. An imaging installation according to claim 18 wherein the processing computer is adapted to obtain optical characteristics of the inside of the sample from the transillumination image, and to obtain the image associating each volumic zone inside the sample with a value of luminescence in said zone from the luminescence image and the optical characteristics.

20. An installation according to claim 1, in which the light reflector device surrounds the support over a solid angle of not less than $\pi$.

21. A luminescence imaging method in which an imaging installation is provided comprising a lightproof enclosure containing:

a support adapted to receive a sample to be imaged;

a detector placed in an acquisition region and adapted to detect a luminescence image of the sample to be imaged; and a light reflector device for reflecting light towards the detector, surrounding the support at least in part, presenting at least two portions that are inclined relative to each other, each reflecting light coming from the sample towards the detector, a processing computer unit connected to the detector and having a memory zone is provided, the support is provided with the sample to be imaged, a locating device emits a light locating signal sweeping all points of the sample, a positioning signal obtained by reflecting the locating signal on each point of the sample and then on the reflector device is detected and stored by the detector in the memory zone, whereby an impulse response of a system for each point of the sample is memorized associated to coordinates of the point in a frame of reference of the imaging installation, the detector detects a luminescence image of the sample to be imaged, corresponding to a light signal emitted from inside the sample, there is obtained, for each geometrical zone of the sample, a luminescence value for said zone from the impulse responses and the detected luminescence image.

22. A luminescence imaging method according to claim 21, in which the positioning images are periodically updated by detection of positioning signals simultaneously with acquiring the luminescence signal.

23. A luminescence imaging method according to claim 21 wherein the memory zone contains a transillumination image previously obtained by detecting a transmitted light signal obtained by scattered transmission of a transillumination light signal applied onto at least one point of the sample;

wherein an image associating each volumic zone inside the sample with a value of luminescence in said zone is obtained from the detected luminescence image and the transillumination image.

24. A luminescence imaging method according to claim 23 wherein, prior to acquiring the luminescence signal, a transmitted signal obtained by scatterly transmitting inside the sample a transillumination signal applied onto at least one point of the sample is detected and stored in the memory zone.

25. A luminescence imaging method according to claim 24 wherein a transillumination signal is generated onto at least one point of the sample, the transillumination signal exciting fluorescence of fluorescent probes contained inside the sample, said fluorescence generating the luminescence signal.

26. Luminescence imaging method according to claim 21, wherein a three-dimensional surfacic envelope of the sample is obtained from the positioning signals.

27. A computer program tangibly embodied on a computer readable medium, and adapted, when executed on a programmable device, to implement a method comprising obtaining, for each geometrical zone of a sample to be imaged, a luminescence value for said zone from previously acquired positioning images, corresponding to the detection of positioning signals obtained by the reflection of a swept locating signal by a respective point of the sample and then by a reflector device at least in part surrounding the sample and presenting at least two portions that are inclined relative to each other and each reflecting light coming from the sample toward a detector, and from a luminescence image of the sample corresponding to a light signal emitted from within the sample.

* * * * *